(12) United States Patent
Nishiura

(10) Patent No.: US 7,577,281 B2
(45) Date of Patent: Aug. 18, 2009

(54) MEDICAL KINEMATIC ANALYSIS APPARATUS AND A MEDICAL KINEMATIC ANALYSIS METHOD

(75) Inventor: Masahide Nishiura, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 606 days.

(21) Appl. No.: 11/203,064

(22) Filed: Aug. 15, 2005

(65) Prior Publication Data
US 2006/0058618 A1    Mar. 16, 2006

(30) Foreign Application Priority Data
Aug. 30, 2004   (JP)   ............... 2004-250465

(51) Int. Cl.
G06K 9/00   (2006.01)
A61B 5/05   (2006.01)
(52) U.S. Cl. ...................... 382/128; 600/407
(58) Field of Classification Search ................ 382/107, 382/128; 600/437, 407
See application file for complete search history.

(56) References Cited

U.S. PATENT DOCUMENTS

| 4,337,661 | A | * | 7/1982 | Kretz | ........................ 600/440 |
| 5,239,591 | A | * | 8/1993 | Ranganath | .................. 382/128 |
| 6,859,548 | B2 | | 2/2005 | Yoshioka et al. | |
| 2003/0171668 | A1 | * | 9/2003 | Tsujino et al. | .............. 600/407 |
| 2005/0111717 | A1 | | 5/2005 | Yoshioka et al. | |

FOREIGN PATENT DOCUMENTS

| CN | 1442118 | 9/2003 |
| JP | 10-99334 | 4/1998 |
| JP | 2003-250804 | 9/2003 |
| JP | 2003-265480 | 9/2003 |

OTHER PUBLICATIONS

Masahide Nishiura et al., "Active Contour Extraction Method Using Partial Shape Constraint Contour Model", IEICE (The Institute of Electronics, Information and Communication Engineers) vol. J83-D-II No. 1, Jan. 25, 2000, pp. 183-190.

* cited by examiner

Primary Examiner—Aaron W Carter
(74) Attorney, Agent, or Firm—Oblon, Spivak, McClelland, Maier & Neustadt, P.C.

(57) ABSTRACT

A medical kinematic analysis apparatuses includes a tracking point coordinate acquiring unit to generate coordinate time series data representing a coordinate of a tracking point on a heart from the time series image data, a motion information acquiring unit to generate time series motion information of the tracking point from the coordinate time series data, a first motion component computation unit to compute a motion component of a cardiac systole/diastolic direction from the time series motion information, and a second motion component computation unit to compute a motion component of a direction different from the cardiac systole/diastolic direction from the time series motion information.

12 Claims, 8 Drawing Sheets

MEDICAL KINEMATIC ANALYSIS APPARATUS AND A MEDICAL KINEMATIC ANALYSIS METHOD

CROSS-REFERENCE TO RELATED APPLICATIONS

This application is based upon and claims the benefit of priority from prior Japanese Patent Application No. 2004-250465, filed Aug. 30, 2004, the entire contents of which are incorporated herein by reference.

BACKGROUND OF THE INVENTION

1. Field of the Invention

The present invention relates to a medical kinematic analysis apparatus and a medical kinematic analysis method, particularly a medical kinematic analysis apparatus and a medical kinematic analysis method, which provide a cardiac motion component different in a direction from a systole/diastolic direction such as twist or rotation along with a cardiac motion component of the systole/diastolic direction.

2. Description of the Related Art

A medical kinematic analysis apparatus to measure a cardiac motion in precision from time-series image data obtained by capturing a heart as a subject, and analyze it for early diagnosis of cardiac disease such as myocardial infarction and stenocardia (refer to Japanese Patent Laid-Open No. 10-99334 (4th page, FIG. 2)).

The typical motion of cardiac ventricular walls can be divided into a cardiac motion in a systole/diastolic direction and a motion due to twist or rotation (motion in a direction different from the systole/diastolic direction). The cardiac motion in the systole/diastolic direction is a motion accomplished by myocardial systole. Therefore, when aberration is found in the motion, this leads often to early diagnosis of, for example, myocardial infarction.

Generally, the cardiac motion in the systole/diastolic direction is larger than the cardiac motion due to twist or rotation. Therefore, a conventional medical kinematic analysis apparatus aims to measure and analyze a cardiac motion component of the systole/diastolic direction (refer to Japanese Patent Laid-Open No. 2003-265480 (3rd page, FIG. 1)).

In a certain cardiac region, the anomaly of the cardiac motion may appear in the motion due to twist or rotation more subtly than in the motion in the cardiac systole/diastolic direction. In such a region, to detect a motion component different in direction from the systole/diastolic, such as cardiac twist or rotation, may be effective in diagnosis. However, the conventional medical kinematic analysis apparatus could not measure or analyze the motion due to twist or rotation along with the motion in the cardiac systole/diastolic direction.

The conventional medical kinematic analysis apparatus could not derive the motion component different in direction from that in the cardiac systole/diastolic direction, such as twist or rotation, along with the cardiac motion component of the cardiac systole extension direction.

It is an object of the present invention to provide a medical kinematic analysis apparatus, and a medical kinematic analysis method of making it possible to acquire a cardiac motion component effective for diagnosis in the direction other than the systole/diastolic direction, such as twist or rotation along with a cardiac motion component of the cardiac systole/diastolic direction.

BRIEF SUMMARY OF THE INVENTION

An aspect of the present invention provides a medical kinematic analysis apparatuses analyzing a cardiac motion from time series image data obtained by capturing a heart, comprising: a tracking point coordinate acquiring unit configured to generate coordinate time series data representing a coordinate of a tracking point on a heart from the time series image data; a motion information acquiring unit configured to generate time series motion information of the tracking point from the coordinate time series data; a first motion component calculating unit configured to compute a motion component of a cardiac systole/diastolic direction from the time series motion information; and a second motion component calculating unit configured to compute a motion component of a direction different from the cardiac systole/diastolic direction from the time series motion information.

DETAILED DESCRIPTION OF THE INVENTION

There will be explained an embodiment of the following, the present invention.

First Embodiment

Figure 1:
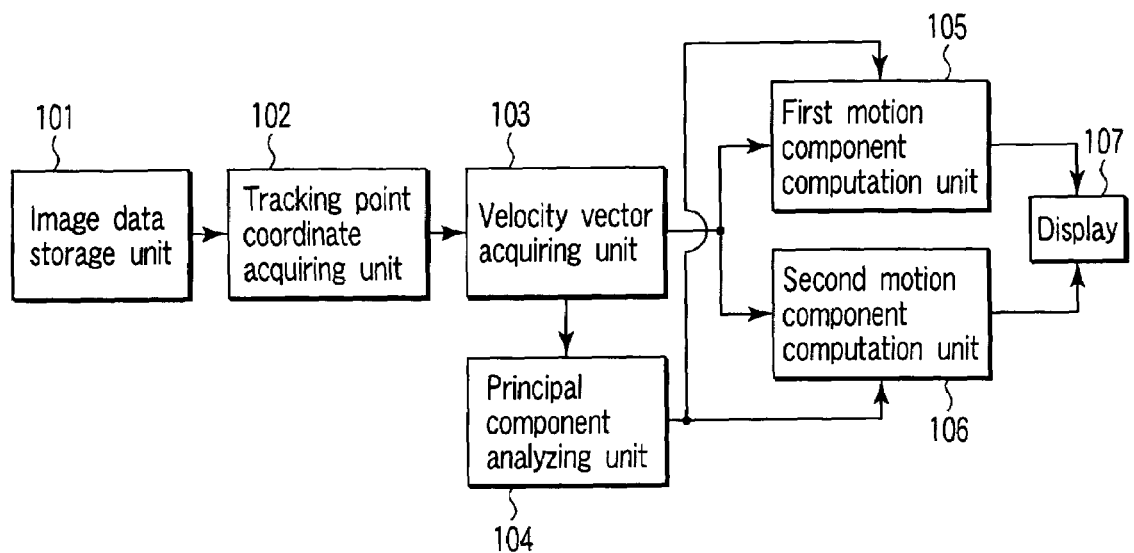
FIG. 1 is a block diagram of a medical kinematic analysis apparatus concerning the first embodiment of the present invention.

FIG. 1 is a block diagram of a medical kinematic analysis apparatus concerning the first embodiment of the present invention.

According to the medical kinematic analysis apparatus concerning the first embodiment, an image data storage unit 101 is configured to store time-series image data obtained by capturing a heart as a subject. A tracking point coordinate acquiring unit 102 is configured to acquire coordinate time series data representing a coordinate of the tracking point on the heart from the time-series image data stored in the image data storage unit 101. A velocity vector acquiring unit 103 is configured to acquire time-series data of a velocity vector of the tracking point as time-series motion information from the coordinate time-series data which is acquired with the tracking point coordinate acquiring unit 102. A principal component analyzing unit 104 is configured to subject the time-series motion information acquired with the velocity vector acquiring unit 103 to principal component analysis.

A first motion component computation unit 105 is configured to compute, as a motion component of a cardiac systole/diastolic direction, a motion component of the first component direction (principal component direction) provided with the principal component analyzing unit 104 from the time-series motion information (i.e., velocity vector of the tracking point) provided with the velocity vector acquiring unit 103. A second motion component computation unit 106 is configured to compute, as a motion component of a direction such as twist or rotation of the heart, a motion component of the second component direction provided with the principal component analyzing unit 104 from the time-series motion information provided with the velocity vector acquiring unit 103. A display unit 107 displays the motion components provided with the first and second motion component computation units 105 and 106, that is, cardiac systole/diastolic component and twist or rotation component.

Figure 2:
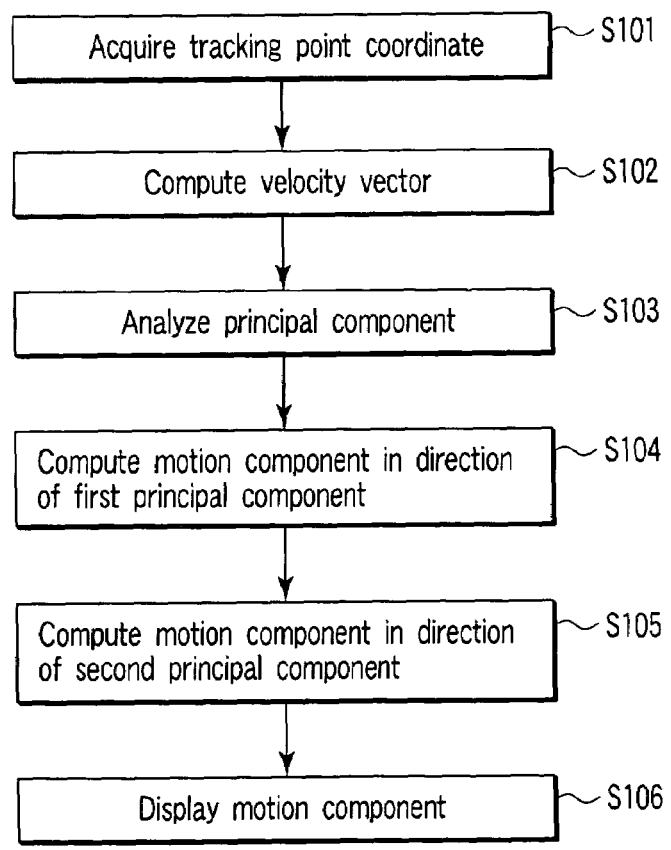
FIG. 2 is flowchart for explaining an operation of the medical kinematic analysis apparatus of the first embodiment.

The medical kinematic analysis apparatus concerning the first embodiment of the present invention will be described referring to FIGS. 1 and 2. FIG. 2 is flowchart for explaining the medical kinematic analysis apparatus concerning the first embodiment of the present invention.

The image data storage unit 101 stores time-series image data obtained by capturing a heart as a subject. The image data stored in the image data storage unit 101 can be acquired with an imaging measure such as ultrasonic diagnostic equipment, MRI, CT. The image data storage unit 101 can use a semiconductor memory, a hard disk, CD-R, CD-RW, DVD-R, DVD-RAM, DVD-RW, etc.

The time-series image data stored in the image data storage unit 101 is sent to the tracking point coordinate acquiring unit 102.

The tracking point coordinate acquiring unit 102 acquires a tracking point appeared in an image sent from the image data storage unit 101 (step S101). The tracking point is a point to be tracked on the heart which appears on the image. A cardiac contour is detected using a method disclosed by, for example, a document "Nishiura et al. "Active Contour Extraction Method Using Partial Shape Constraint Contour Model", The Transaction of The Institute of Electronics, Information and Communication Engineers, vol. J83-D-II, no. 1, pp. 183-190, January 2000" or U.S. patent: U.S. Pat. No. 6,859,548, B2, the entire contents of which are incorporated herein by reference. The feature points on the contour such as an apical part and a valve ring are detected from the cardiac contour. These points may be assumed to be tracking points. The tracking point may be set manually for each image of every time using a mouse without extracting the cardiac contour.

The tracking point needs not be always one, and a plurality of feature points on the cardiac contour extracted by the above method may be tracking points. However, for brevity, only a single tracking point is described hereinafter.

The tracking point is acquired for each time from time-series image data stored in the image data storage unit 101 by the above method. The coordinate of the tracking point acquired at the time t in this way is expressed by a two-dimensional coordinate (xt, yt). The coordinate (xt, yt) of this tracking point is sent to the velocity vector acquiring unit 103.

The velocity vector acquiring unit 103 computes time-series data of the velocity vector of the tracking point (time-series motion information) from the time-series data of the tracking point coordinate (xt, yt) sent from the tracking point coordinate acquiring unit 102 (step S102).

The velocity vector (vxt, vyt) of the tracking point at the time t can be obtained by, for example, the equation (1).

$$v_{xt} = \frac{x_{t+1} - x_t}{\Delta t} \qquad (1)$$
$$v_{yt} = \frac{y_{t+1} - y_t}{\Delta t}$$

$\Delta t$ is a time interval between time t and time t+1.

The velocity vector (vxt, vyt) is computed from coordinates of tracking points at two consecutive times by the equation (1). However, the velocity vector (vxf, vyf) may be computed from coordinates of the tracking points obtained at a suitable time interval as shown in an equation (2).

$$v_{xt} = \frac{x_{t+1} - x_t}{\Delta t'} \qquad (2)$$
$$v_{yt} = \frac{y_{t+1} - y_t}{\Delta t'}$$

where $\Delta t'$ is a time interval between time t and time t+i.

The time series data of the velocity vector (vxt, vyt) of the tracking point acquired with the velocity vector acquiring unit 103 is sent to the first principal component analyzing unit 104, the first motion component computation unit 105 and the second motion component computation unit 106.

The principal component analyzing unit 104 subjects to the principal component analysis the time series data of the velocity vector (vxt, vyt) of the tracking point, which is sent from the velocity vector acquiring unit 103 to obtain the first and second motion component directions of the tracking point (step S103).

The first and second motion component directions can be obtained by computing an eigenvector of a covariance matrix C settled by an equation (3).

$$C = \frac{1}{n}\sum_{t=1}^{n}\left(V_t - \frac{1}{n}\sum_{i=1}^{n}V_i\right)^T\left(V_t - \frac{1}{n}\sum_{i=1}^{n}V_i\right) \qquad (3)$$

Vt represents the velocity vector (vxt, vyt) and T represents transpose of the vector.

In other words, when the eigenvectors p1 and p2 of the covariance matrix C are defined by an equation (4), p1 is a unit vector representing the first motion component direction of the tracking point (referred to as the first component vector), and p2 is a unit vector representing a second motion component direction (referred to as the second component vector hereinafter).

$$Cp_k = \lambda_k p_k, k=1, 2$$

$$p_k^T p_k 1, \lambda_1 > \lambda_2 \quad (4)$$

In this equation, $\lambda 1$ and $\lambda 2$ represent eigenvalues corresponding to the eigenvectors p1 and p2, respectively.

The first component direction obtained by subjecting the time series vector data to principal component analysis means a direction in which variance of the time series vector data becomes maximum. In the case that the velocity vector data of the cardiac tracking point is used as time series vector data, the direction in which the variance of the velocity vector data becomes maximum is a direction in which the variation of the velocity vector of the tracking point becomes maximum. Accordingly, in many cases, the first component direction obtained by subjecting the time series velocity vector data to principal component analysis is considered to be a cardiac systole/diastolic direction.

On the other hand, since the second component direction is a direction perpendicular to the first component direction, the second component obtained by subjecting the time series velocity vector data to principal component analysis is considered to be a motion direction such as twist or rotation which is perpendicular to the systole/diastolic direction in many cases.

Accordingly, if the motion components in the first and second component directions of the time series data of the velocity vector obtained with the velocity vector acquiring unit 103 are computed and displayed, it is possible to grasp a motion component of the systole/diastolic direction of the velocity vector of the tracking point and a motion component of a direction such as torsion or convolution at the same time.

The principal component analyzing unit 104 sends the first component vector p1 of the velocity vector to the first motion component computation unit 105. Similarly, the principal component analyzing unit 104 sends the second component vector p2 of the velocity vector to the second motion component computation unit 106.

The first motion component computation unit 105 computes the motion component $v_{Mt}$ in the first component direction of the velocity vector Vt sent by the velocity vector acquiring unit 103, using the first component vector p1 of velocity vector sent from principal component analyzing unit 104 (step S104).

The motion component $v_{Mt}$ in the first component direction of the velocity vector Vt can be obtained by computing an inner product of the velocity vector Vt and the first component vector p1 based on an equation (5) every time t.

$$v_{Mt} = V_t \cdot p_1 \quad (5)$$

The motion component $v_{Mt}$ of the first component direction of the velocity vector obtained by an equation (5) is sent to the display unit 107 as time series data.

The second motion component computation unit 106 computes a motion component $v_{St}$ in the second component direction of the velocity vector $V_t$ sent by the velocity vector acquiring unit 103 using the second component vector p2 of the velocity vector sent from the principal component analyzing unit 104 (step S105).

The motion component $v_{St}$ in the second component direction of the velocity vector $V_t$ can be obtained by computing an inner product of the velocity vector $V_t$ and the second component vector p2 based on an equation (6) every time t.

$$v_{St} = V_t \cdot p_2 \quad (6)$$

The motion component $v_{St}$ in the second component direction of the velocity vector obtained by the equation (6) is sent to the display unit 107 as time series data.

The display unit 107 displays motion components $v_{Mt}$ and $v_{St}$ in the first and second component directions of the velocity vector of the tracking point, which are sent from the first and second motion component computation units 105 and 106 (step S106). The display unit 107 can use, for example, a CRT display or a liquid crystal display.

Figure 3:
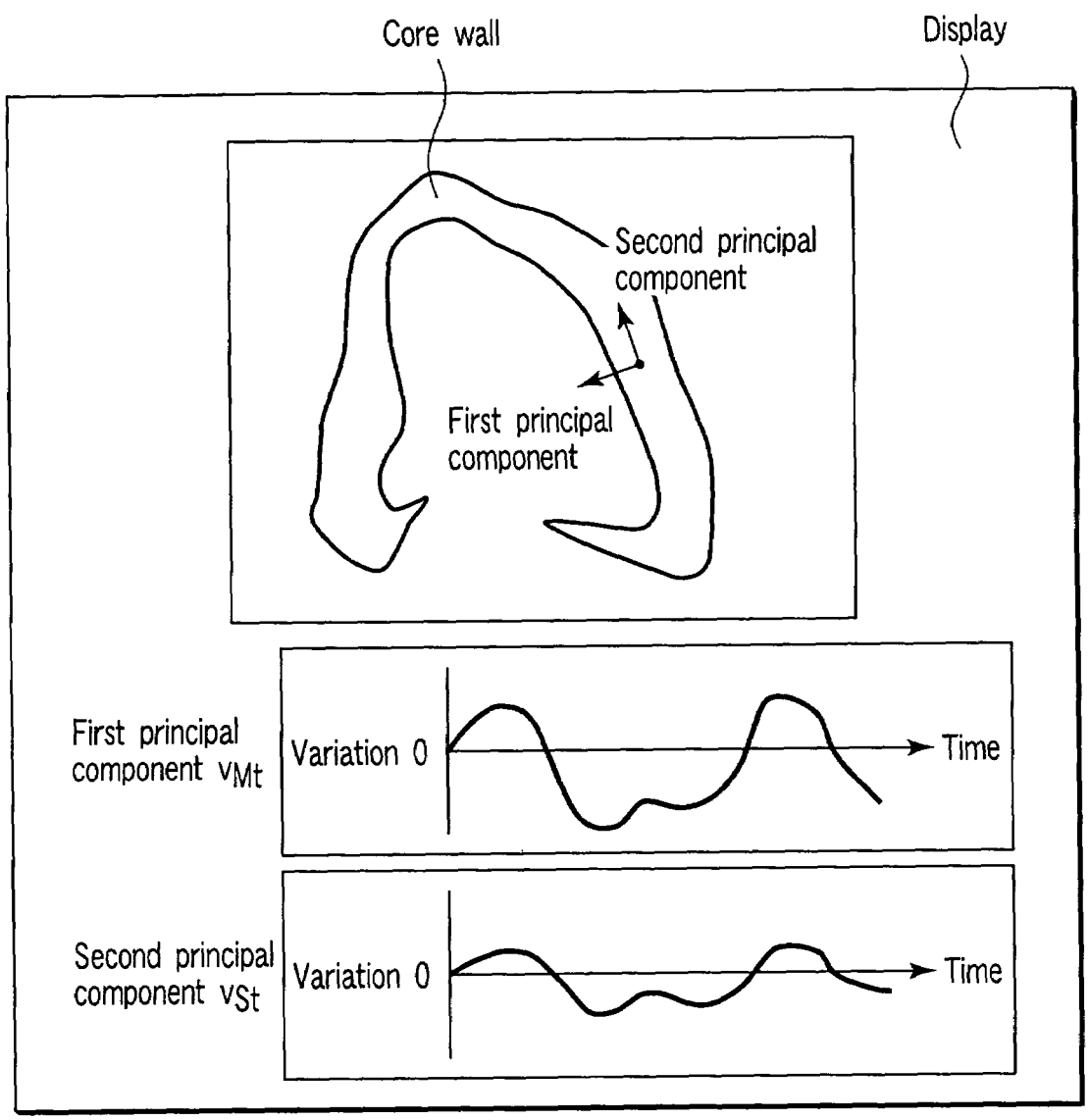
FIG. 3 is a diagram showing an example of a display method of a kinematic component according to the first embodiment of the present invention.

When each motion component is displayed on the display unit 107, each motion component may be displayed as a graph together with display of the first and second component directions of the tracking point on the cardiac image as shown in FIG. 3.

In this way, when the motion components in the first and second component directions of the tracking point are displayed as a graph at the same time, it is possible to observe at the same time the states of the motion of a cardiac systole/diastolic direction and the motion of a direction such as twist or rotation in the tracking point.

As thus described, according to the first embodiment of the present invention, when the velocity vector data of the tracking point is acquired from the image data obtained by capturing a heart as a subject, this velocity vector data is subjected to principal component analysis, and the motions of the first and second component directions are computed and displayed. The motion components in the cardiac systole/diastolic direction and the motion component of the direction such as twist or rotation can be grasped at the same time. This makes it possible to acquire the motion component, which is more effective in diagnosis.

In the embodiment, after the motion component $v_{Mt}$ in the first component direction of the velocity vector $V_t$ is computed with the first motion component computation 105 in step S104, the motion component $v_{St}$ in the second component direction of the velocity vector Vt is computed with the second motion component computation unit 106 in step S105. However, the order to compute the motion components in the first and second component directions may be reversed. In other words, in FIG. 2, the step S105 may be replaced with the step S104. More specifically, at first the motion component $v_{St}$ in the second component direction of the velocity vector Vt is computed with the second motion component computation 106, and then the motion component $v_{Mt}$ in the first component direction of the velocity vector Vt is computed with the first motion component computation unit 105.

In the embodiment, the time series motion information is assumed to be the time series data of the velocity vector of the tracking point. However, the time series data of the displacement vector of the tracking point may be the time series motion information. The displacement vector Dt=(dxt, dyt) of the tracking point can be computed as displacement of a tracking point coordinate between, for example, times t and t+i from the time series data of the coordinate of the tracking point, using an equation (7).

$$d_{xt} = x_{t+i} - x_t$$

$$d_{yt} = y_{t+i} - y_t \quad (7)$$

If the displacement vector Dt of the tracking point obtained by using the equation (7) is subjected to principal component analysis instead of the velocity vector Vt of the tracking point, to obtain motion components of the first and second component directions, the motion component of the systole/diastolic direction of the tracking point and the motion component of the direction such as twist or rotation can be obtained at the same time.

In the embodiment, the cardiac systole/diastolic direction is assumed to be the first component direction obtained by subjecting the time series data of the velocity vector of the tracking point to principal component analysis. However, the first component direction obtained by subjecting time series data of the coordinate of the tracking point to principal component analysis may be used as the cardiac systole/diastolic direction. In other words, it is considered that the direction in which the variance of the time series data of the coordinate of the tracking point becomes maximum is a direction in which the variation of the coordinate of the tracking point becomes maximum. Therefore, this direction can be considered to be a cardiac systole/diastolic direction. Consequently, if the principal component analyzing unit 104 obtains an eigenvector of the covariance matrix C settled by the equation (3) using the coordinate of the tracking point (xt, yt) instead of the velocity vector (vxt, vyt), the first component direction becomes the cardiac systole/diastolic direction, and the second component direction becomes the motion direction such as twist or rotation.

In this way, if the first and second motion component computation units 105 and 106 compute motion components in the systole/diastolic direction and motion direction such as twist or rotation using unit vectors p1 and p2 representing the first and second component directions, and display them on the display unit 107, these motion components in the tracking point can be grasped at the same time.

In the embodiment, the coordinate of the tracking point is assumed to be two-dimensional. However, it is possible that the tracking point coordinate acquiring unit 102 obtains a three-dimensional coordinate of the tracking point from an image provided with a measure such as an ultrasonic diagnostic equipment, MRI, CT, and the velocity vector acquiring unit 103 obtains a velocity vector using the three-dimensional coordinate.

In the embodiment, the display unit 107 displays the first and second component directions of the tracking point, and the motion components $v_{Mt}$, $v_{St}$ in the first and second component directions of the velocity vector Vt in a graph as shown in FIG. 3. As described above, the first component direction obtained by subjecting the time series velocity vector data of the tracking point to principal analysis is considered to be a cardiac systole/diastolic direction. In a certain cardiac region, the variation of the velocity vector in the cardiac systole/diastolic direction may be larger than that of the velocity vector of the motion direction such as twist or rotation. In such a region, the first component direction obtained by subjecting the time series velocity vector data of the tracking point to principal component analysis represents a motion direction such as cardiac twist or rotation, and the second component direction represents a cardiac systole/diastolic direction.

Figure 4:
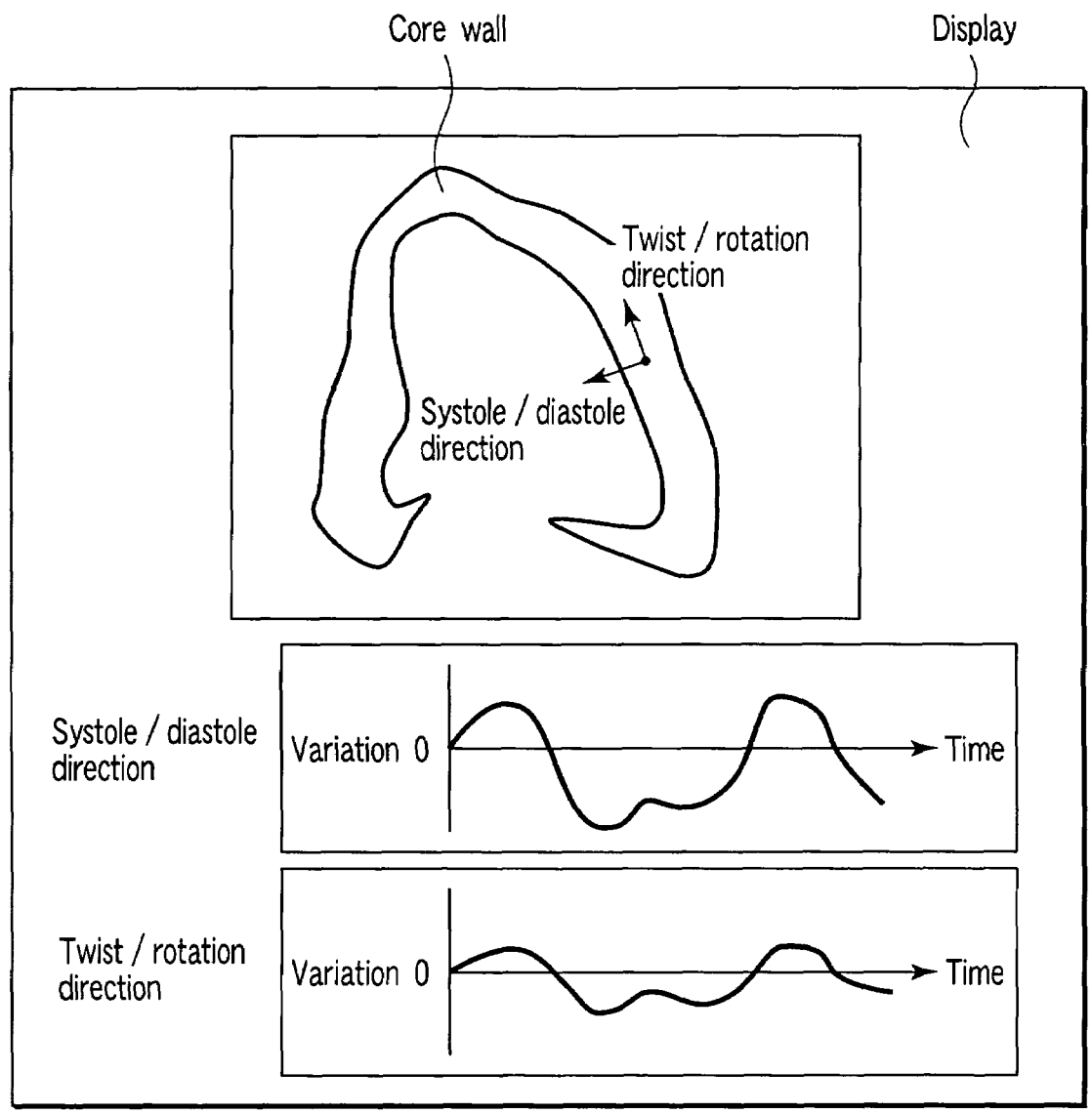
FIG. 4 is a diagram showing an example of a display method of a kinematic component according to the first embodiment of the present invention.

Consequently, the principal component analyzing unit 104 obtains the first and second component vectors p1 and p2 of the tracking point, and then detects whether the motion direction expressed by each vector is a cardiac systole/diastolic direction or a motion direction such as twist or rotation. The display unit 107 displays the motion component of the velocity vector of the tracking point correlating with the cardiac systole/diastolic and the twist or rotation as shown in FIG. 4.

It is possible by such a display to grasp easily motion components in the cardiac systole/diastolic direction and the motion direction such as twist or rotation, irrespective of a region of the heart.

Figure 5A:
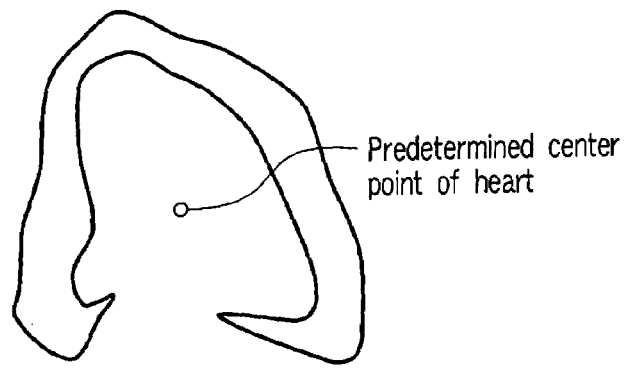
FIGS. 5A to 5C are diagrams for explaining a relation between a motion composition of a tracking point and a motion direction according to the first embodiment of the present invention.
Figure 5B:
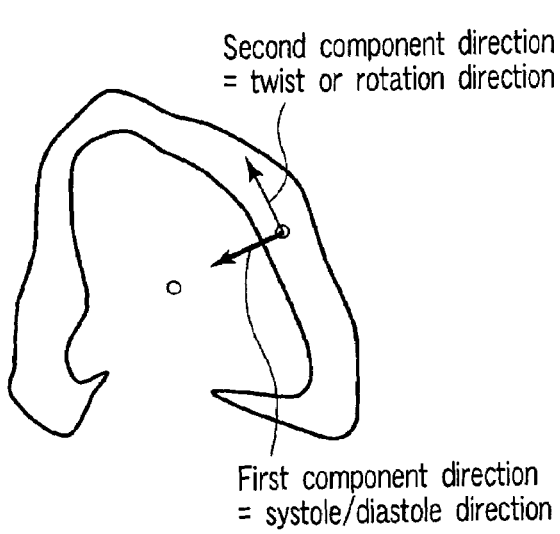
Figure 5C:
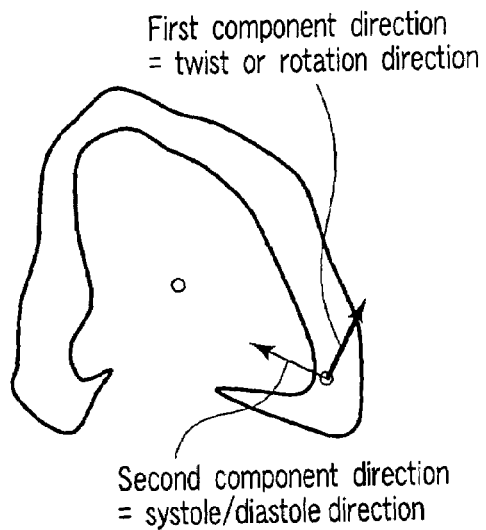

In the case of determining whether the motion direction represented by the first and second component vectors of the velocity vector of the tracking point is a cardiac systole/diastolic direction or a motion direction such as twist or rotation, a center point of the heart is set beforehand as shown in FIG. 5A, and a vector of a direction toward this center point of the heart may be determined as a cardiac systole/diastolic direction. FIGS. 5B and 5C show examples, which detect by this method whether the motion direction represented by each vector is a cardiac systole/diastolic direction or a motion direction such as twist or rotation.

FIG. 5B shows an example that the direction in which the variation of the velocity vector of the tracking point becomes maximum is a cardiac systole/diastolic direction, and the direction of the first component vector obtained by subjecting the velocity vector data of tracking point to principal component analysis becomes a cardiac systole/diastolic direction.

On the other hand, FIG. 5C shows an example that the direction in which the variation of the velocity vector of the tracking point becomes maximum is a motion direction such as twist or rotation of the heart, and the direction of the first component vector obtained by subjecting the time series velocity vector data of the tracking point to principal component analysis becomes a motion direction such as twist or rotation of the heart.

In the embodiment, the motion components $v_{Mt}$ and $v_{St}$ in the first and second component directions of the velocity vector of the tracking point, which are computed with the first and second motion component computation units 105 and 106, respectively, are displayed on the display unit 107. These data may be stored in a memory medium without displaying on the display unit 107, and analyzed with another data processor or data processing software.

In the embodiment, as shown in FIG. 3, the motion components $v_{Mt}$ and $v_{St}$ in the first and second component directions of the velocity vector of the tracking point are displayed on the display unit 107 as a graph at the same time. However, these motion components may be displayed on display unit 107 individually by providing a measure for switching the display. In this case, it becomes possible to grasp individually the motion in the cardiac systole/diastolic direction and the motion in the direction such as twist or rotation.

This medical kinematic analysis apparatus can be realized using, for example, a general-purpose computer equipment as basic hardware. In other words, the tracking point coordinate acquiring unit 102, velocity vector acquiring unit 103, principal component analyzing unit 104, first motion component computation unit 105 and second motion component computation unit 106 can be realized by making a processor mounted in the computer equipment execute a program. In this time, the medical kinematic analysis apparatus may be realized by installing the program in the computer equipment beforehand, or may be implemented by installing the program stored in a memory medium such as a compact disk-read only memory or the program distributed through a network, in the computer equipment appropriately. The image data storage unit 101 can be realized by a memory, a hard disk or a memory medium such as CD-R, CD-RW, DVD-RAM, DVD-R, which is built-in the computer equipment or attached thereto. The display unit 107 can use a display device such as a display built-in the computer equipment or attached thereto.

Second Embodiment

In the first embodiment, the time series data of the velocity vector of the tracking point is subjected to principal component analysis to obtain first and second component directions, and the first component direction is assumed to be a cardiac systole/diastolic direction and the second component direction is assumed to be a motion directions such as a cardiac twist or rotation.

In the second embodiment, at first, a cardiac contour is extracted. The normal direction of the contour is assumed to be a motion direction of a cardiac systole/diastolic, and the tangential direction of the contour is assumed to be a motion direction such as cardiac twist or rotation. There will be explained a method of acquiring the motion component of the tracking point in these directions.

Figure 6:
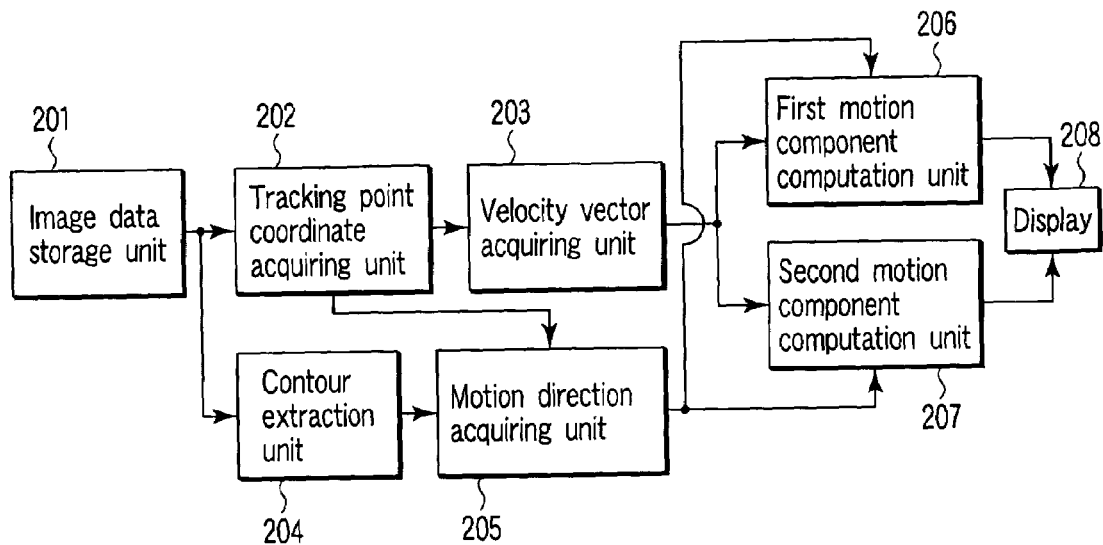
FIG. 6 is a block diagram of a medical kinematic analysis apparatus concerning the second embodiment of the present invention.

FIG. 6 is a block diagram of a medical kinematic analysis apparatus concerning the second embodiment of the present invention.

According to the medical kinematic analysis apparatus concerning the second embodiment, an image data storage unit 201 is configured to store time-series image data obtained by capturing a heart as a subject. A tracking point coordinate acquiring unit 202 is configured to acquire time series image data of a coordinate of the tracking point on the heart from the time-series image data stored in the image data storage unit 201. A velocity vector acquiring unit 203 is configured to acquire time-series data of a velocity vector of the tracking point as time-series motion information from the time-series data of a coordinate of the tracking point which is acquired with the tracking point coordinate acquiring unit 202.

A contour extraction unit 204 is configured to extract a cardiac contour from the time series image data stored in the image data storage unit 201. A motion direction acquiring unit 205 is configured to acquire, from the cardiac contour extracted with the contour extraction unit 204, motion directions of normal and tangential directions with respect to the contour at the tracking point. A first motion component computation unit 206 is configured to compute the motion component of the normal direction with respect to the contour, which is acquired with the motion direction acquiring unit 205, from the velocity vector of the tracking point which is acquired with the velocity vector acquiring unit 203, thereby to obtain a motion component of the cardiac systole/diastolic direction.

A second motion component computation unit 207 is configured to compute the motion component of the tangential direction with respect to the contour, which is acquired with the motion direction acquiring unit 205, from the velocity vector of the tracking point which is acquired with the velocity vector acquiring unit 203, thereby to obtain a motion component of a direction such as cardiac twist or rotation. A display unit 208 displays the motion components obtained by the first and second motion component computation units 206 and 207.

There will be explained an operation of a medical kinematic analysis apparatus concerning the second embodiment of the present invention. The second embodiment differs from the first embodiment in that the contour extraction unit 204 and the motion direction acquiring unit 105 are provided instead of the principal component analyzing unit 104 of the first embodiment. Accordingly, like structural elements (image data storage unit 201, tracking point coordinate acquiring unit 202 and velocity vector computation unit 203) corresponding to those (image data storage unit 101, tracking point coordinate acquiring unit 102 and velocity vector computation unit 103) like in the first embodiment are omitted from explanation.

The contour extraction unit 204 extracts a cardiac contour from the image data stored in the image data storage unit 201. A method of extracting a cardiac contour can use a method disclosed by, for example, a document "Nishiura et al. "Active Contour Extraction Method Using Partial Shape Constraint Contour Model", The Transaction of The Institute of Electronics, Information and Communication Engineers, vol. J83-D-II, no. 1, pp. 183-190, January 2000", the entire contents of which are incorporated herein by reference. A device such as a mouse or key-board which can trace a contour of the heart manually may be provided to set the contour manually.

Assume that extraction of the contour is done on the cardiac end-diastolic image data among the time series image data stored in the image data storage unit 201 in the present embodiment.

The contour extraction unit 204 sends the extracted cardiac end-diastolic contours to the motion direction acquiring unit 205.

The motion direction acquiring unit 205 acquires motion components of normal and tangential directions with respect to the contour at the tracking point from the cardiac end-diastolic contours sent from the contour extraction unit 204. Assume that the normal and tangential directions of the contour are normal and tangential directions with respect to the center line obtained from the cardiac end-diastolic contours at a point on the center line as shown in FIG. 7.

Figure 7:
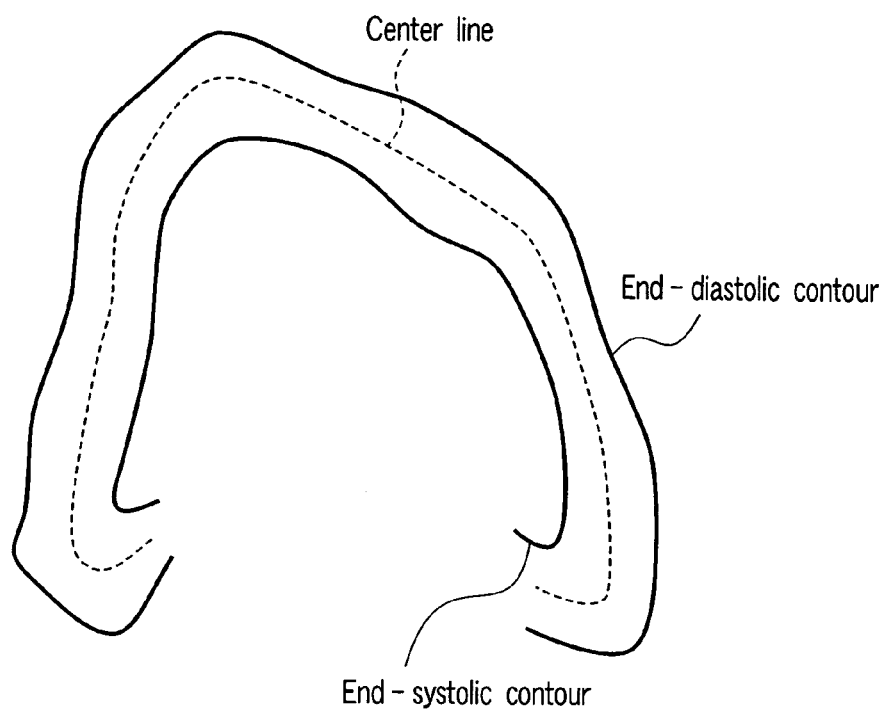
FIG. 7 is a diagram showing a cardiac contour (center line) according to the second embodiment of the present invention.

The motion direction acquiring unit 205 obtains a center line between the cardiac end-diastolic contours sent from the contour extraction pars 204 as shown in FIG. 7.

The motion direction acquiring unit 205 searches for a coordinate on the center line from the time series data of the tracking point coordinate provided with the tracking point coordinate acquiring unit 202. If the coordinate of the center line does not exist in the tracking point coordinates provided with the tracking point coordinate acquiring unit 202, the motion direction acquiring unit 205 searches for a point on the center line which is nearest to the tracking point coordinate. If the tracking point coordinate at time t is (xt, yt), the point (xc, yc) on the center line which is nearest to the tracking point coordinate can be computed as a point (xc, yc) to satisfy, for example, an equation (8):

$$\min_{(x_c, y_c), (x_t, y_t)} \sqrt{(x_c - x_t)^2 + (y_c - y_t)^2} \quad (8)$$

Figure 8:
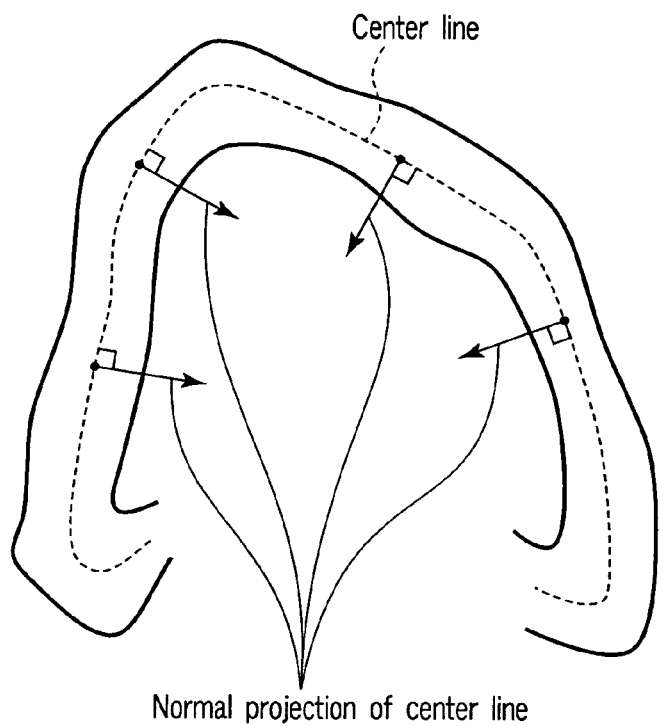
FIG. 8 is a diagram showing a normal projection of the contour of a heart according to the second embodiment of the present invention.
Figure 9:
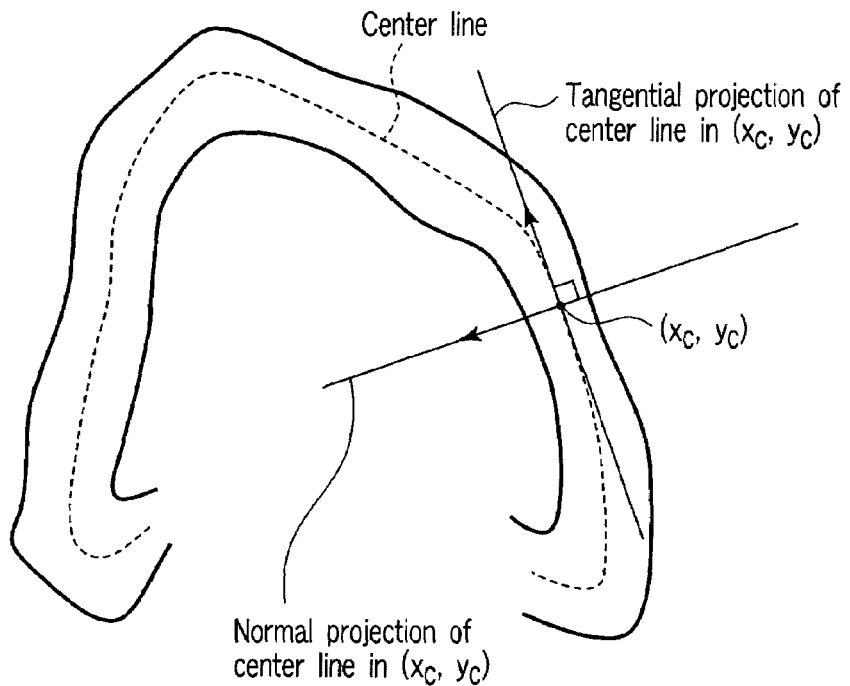
FIG. 9 is a diagram showing a normal projection and tangential projection of the contour of a heart according to the second embodiment of the present invention.
Figure 10:
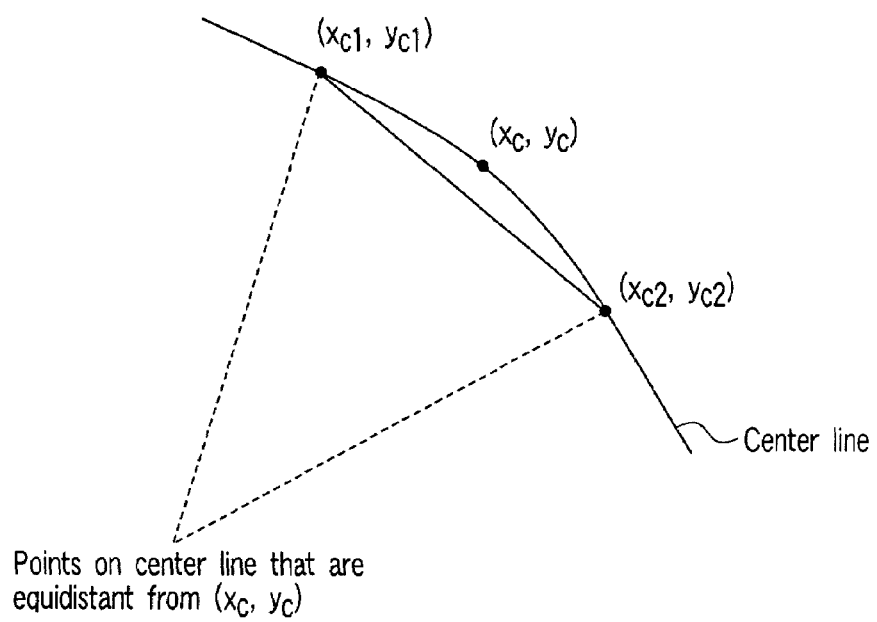
FIG. 10 is a diagram for explaining a method of computing a unit vector of a normal projection and tangential projection according to the second embodiment of the present invention.

It can be considered that motion of the normal direction with respect to the center line at each point on the center line is motion of the cardiac systole/diastolic direction as shown in FIG. 8. The motion direction acquiring unit 205 acquires unit vectors of the normal and tangential directions about the point $(x_c, y_c)$ on the center line as shown in FIG. 9. If the motion component of the tracking point in these directions is acquired, it becomes possible to obtain approximately the motion components of the systole/diastolic direction of the tracking point and a direction such as twist or rotation thereof.

The unit vectors r1 and r2 of the normal and tangential directions concerning a point $(x_c, y_c)$ on the center line can be obtained from points $(x_{c1}, y_{c1})$ and $(x_{c2}, y_{c2})$ at a predetermined distance from the point $(x_c, y_c)$ on the center line, using an equation (9).

$$\text{Normal direction } r1 = \left(\frac{y_{c1} - y_{c2}}{N}, \frac{-x_{c1} + x_{c2}}{N}\right) \quad (9)$$

$$\text{Tangential direction } r2 = \left(\frac{x_{c1} - x_{c2}}{N}, \frac{y_{c1} - y_{c2}}{N}\right)$$

$$N = \sqrt{(x_{c1} - x_{c2})^2 + (y_{c1} - y_{c2})^2}$$

The motion direction acquiring unit 205 sends the first unit vector r1 representing the normal direction of the cardiac contour obtained in this way to the motion component computation unit 206, and the second unit vector r2 representing the tangential direction of the cardiac contour to the motion component computation unit 207.

The first motion component computation unit 206 computes a motion component $v_{Mt}$ of the normal direction with respect to the cardiac contour and of the velocity vector Vt sent from the velocity vector acquiring unit 203, using the unit vector r1 of the normal direction with respect to the cardiac contour sent from the motion direction acquiring unit 205.

The motion component $v_{Mt}$ of the normal direction with respect to the cardiac contour can be acquired by computing an inner product of the velocity vector Vt and the unit vector r1 every time t based on an equation (10).

$$v_{Mt} = V_t \cdot r1 \qquad (10)$$

Similarly, the second motion component computation unit 207 computes a motion component $v_{Mt}$ of the tangential direction with respect to the cardiac contour and of the velocity vector Vt sent from the velocity vector acquiring unit 203, using the unit vector r1 of the tangential direction with respect to the cardiac contour sent from the motion direction acquiring unit 205.

The motion component $v_{St}$ of the normal direction with respect to the cardiac contour can be acquired by computing an inner product of the velocity vector Vt and the unit vector r2 every time t based on an equation (11).

$$v_{St} = V_t \cdot r2 \qquad (11)$$

The motion components $v_{Mt}$ and $v_{St}$ of the normal and tangential directions with respect to the cardiac contour of the tracking point, which are computed by the equations (10) and (11) are displayed on the display unit 208. The motion component of the cardiac systole/diastolic direction and the motion component of the direction such as twist and rotation can be grasped at the same time by this display.

As thus described, according to the second embodiment of the present invention, the velocity vector data of the tracking point is acquired from the image data obtained by capturing a heart as a subject, and the motion components of the velocity vector data in the normal and tangential directions with respect to the cardiac contour are computed and displayed. As a result, the motion component of the cardiac systole/diastolic direction and the motion component of the direction such as twist or rotation can be grasped at the same time, whereby the motion component which is more effective in diagnosis can be obtained.

The above embodiment assumes that the normal and tangential directions of the center line settled from the cardiac end-diastolic contours are the normal and tangential directions with respect to the cardiac contour respectively. However, it is possible to extract the cardiac contour from the time series image data stored in the image data storage unit 201 for each time and acquire the normal and tangential directions from the contour for each time. In this case, a point which is nearest to a coordinate of the tracking point of a time is detected from among points on the contour which are extracted for each time, and the normal and tangential directions with respect to the contour at that point may be assumed as the systole/diastolic direction of the tracking point and the motion direction such as twist or rotation, respectively.

Third Embodiment

In the first embodiment, the time series data of the velocity vector of the tracking point is subjected to principal component analysis, and the first component direction is set to be the cardiac systole/diastolic direction. Further, in the second embodiment, the cardiac contour is extracted, and the normal direction of the contour is set to be the cardiac systole/diastolic.

Figure 11:
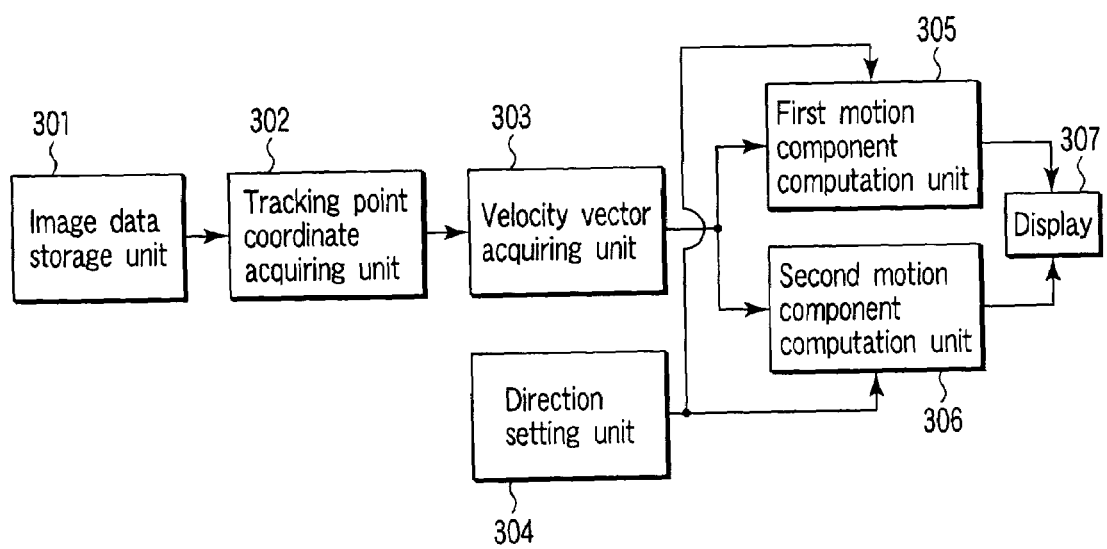
FIG. 11 is a block diagram of a medical kinematic analysis apparatus concerning the third embodiment of the present invention.

In the third embodiment, there will be explained a method of computing a motion component of a systole/diastolic direction and a motion component of a direction such as twist or rotation based on a manually set cardiac systole/diastolic direction. FIG. 11 is a block diagram of a medical kinematic analysis apparatus concerning the third embodiment of the present invention.

According to the medical kinematic analysis apparatus concerning the third embodiment, an image data storage unit 301 is configured to store time-series mage data obtained by capturing a heart as a subject. A tracking point coordinate acquiring unit 302 is configured to acquire time series image data of a coordinate of the tracking point on the heart from the time-series image data stored in the image data storage unit 301. A velocity vector acquiring unit 303 is configured to acquire time-series data of a velocity vector of the tracking point as time-series motion information from the time-series data of a coordinate of the tracking point which is acquired with the tracking point coordinate acquiring unit 302.

A direction setting unit 304 is configured to set a cardiac systole/diastolic direction in the tracking point. A first motion component computation unit 305 is configured to compute a motion component of a cardiac systole/diastolic direction set by the direction setting unit 304 from the velocity vector of tracking point provided with the velocity vector acquiring unit 303. A second motion component computation unit 306 is configured to compute a motion component of a direction perpendicular to the cardiac systole/diastolic direction set by the direction setting unit 304 from the velocity vector of the tracking point provided with the velocity vector acquiring unit 303. A display unit 107 displays motion components provided with the first motion component computation unit 305 and the second motion component computation unit 306.

There will be explained an operation of the medical kinematic analysis apparatus concerning the third embodiment of the present invention. The third embodiment differs from the first embodiment in that the direction setting unit 304 setting a cardiac systole/diastolic direction in the tracking point is provided instead of the principal component analyzing unit 104 of the first embodiment. Accordingly, like structural elements (image data storage unit 301, tracking point coordinate acquiring unit 302 and velocity vector computation unit 303) corresponding to those (image data storage unit 101, tracking point coordinate acquiring unit 102 and velocity vector computation unit 103) like in First embodiment are omitted from explanation.

Figure 12:
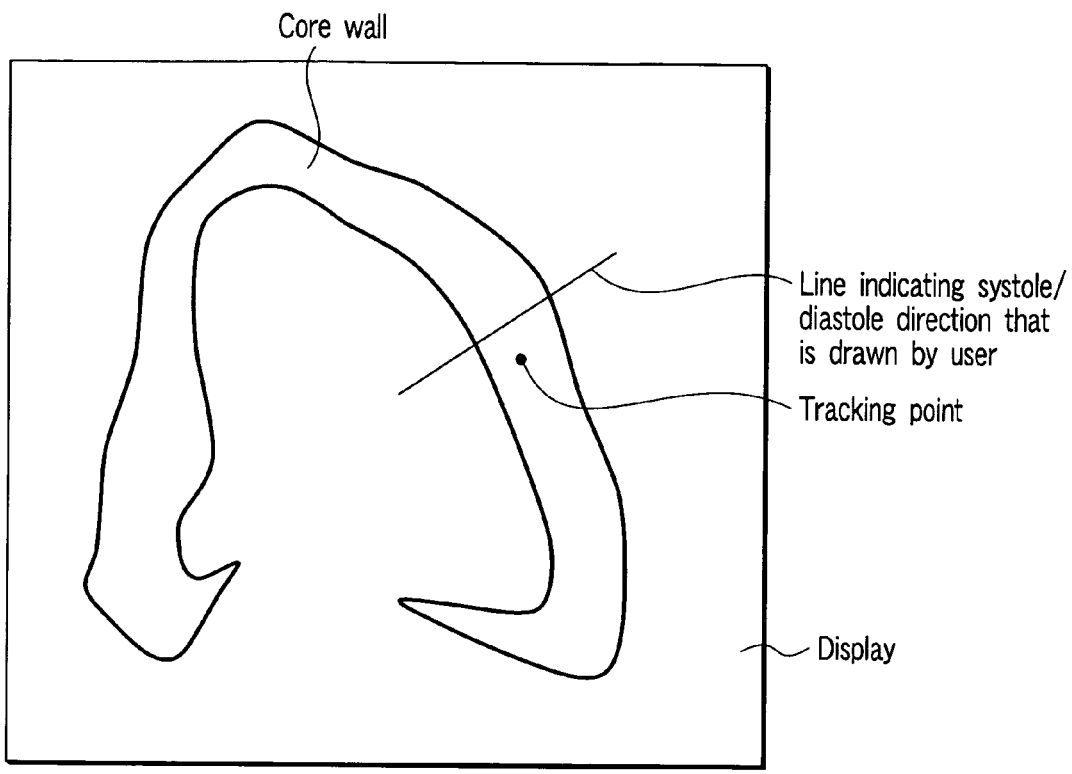
FIG. 12 is a diagram for explaining a method of setting a cardiac systole/diastolic direction concerning the third embodiment of the present invention.

The direction setting unit 304 sets a systole/diastolic direction of the tracking point manually. In setting a direction with the direction setting unit 304, a user draws, on the display displaying a heart, a line in a direction conceivable to be a systole/diastolic direction with a mouse or a keyboard as shown in FIG. 12.

Figure 13:
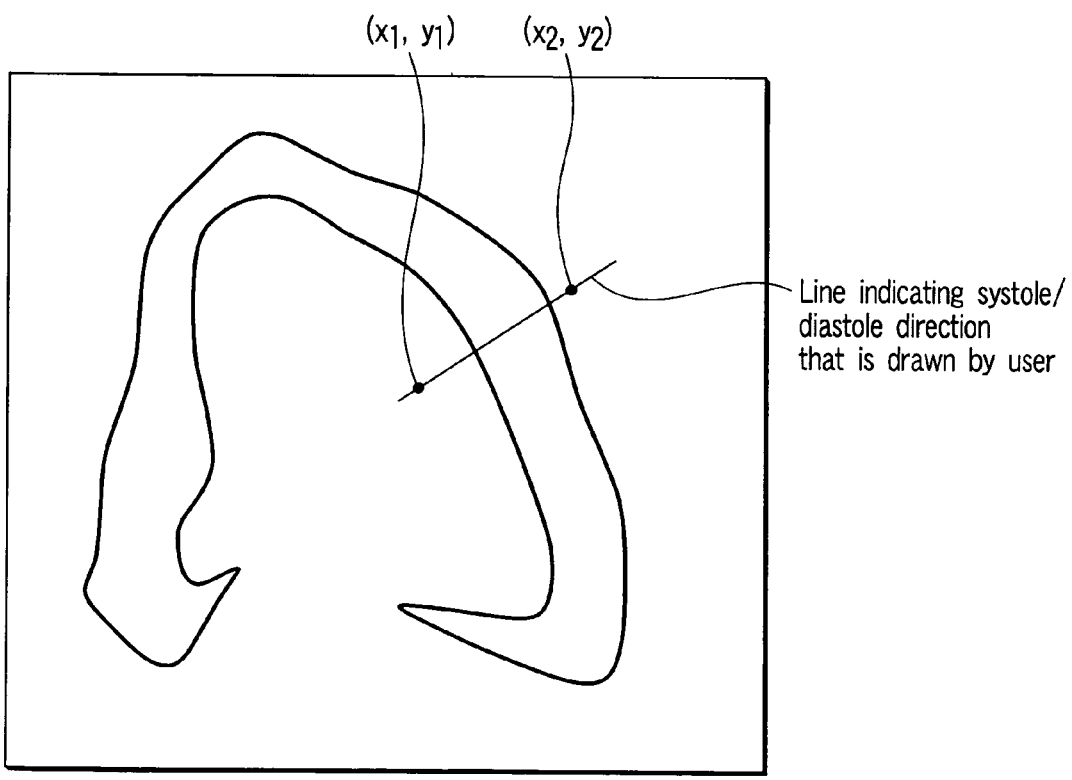
FIG. 13 is a diagram for explaining a method of computing a unit vector of a normal line direction and a tangential direction concerning the third embodiment of the present invention.

The direction setting unit 304 computes a unit vector m1 indicating a cardiac systole/diastolic direction from a line drawn in this way. The unit vector m1 indicating the cardiac systole/diastolic direction can be obtained by an equation (12) from two points (x1, y1) and (x2, y2) on the line drawn by the user as shown in FIG. 13.

$$m_1 = \left(\frac{x_1 - x_2}{N}, \frac{y_1 - y_2}{N}\right) \quad (12)$$

where $N = \sqrt{(x_1 - x_2)^2 + (y_1 - y_2)^2}$

Further, the direction setting unit 304 obtains a unit vector m2 of a direction perpendicular to the cardiac systole/diastolic direction, namely a motion direction such as twist or rotation from two points (x1, y1) and (x2, y2) by an equation (13).

$$m_2 = \left(\frac{y_1 - y_2}{N}, \frac{-x_1 + x_2}{N}\right) \quad (13)$$

where $N = \sqrt{(x_1 - x_2)^2 + (y_1 - y_2)^2}$

The unit vector $m_1$ of the cardiac systole/diastolic direction and the unit vector $m_2$ of the direction perpendicular to the cardiac systole/diastolic direction are sent to the first and second motion component computation units 305 and 306, respectively.

The first and second motion component computation units 305 and 306 compute a motion component of a systole/diastolic direction of the velocity vector of the tracking point sent from the velocity vector acquiring unit 303 and a motion component of a direction such as twist or rotation thereof, using the unit vectors m1 and m2 sent from direction setting unit 304, respectively.

The motion component of the systole/diastolic direction of the velocity vector of the tracking point can be computed by obtaining an inner product of the velocity vector of the tracking point and the unit vector $m_1$ of the cardiac systole/diastolic direction. The motion component of a direction such as twist or rotation of the velocity vector of the tracking point can be computed by obtaining an inner product of the velocity vector of the tracking point and the unit vector $m_2$ of the direction such as twist or rotation.

The computed motion component of the systole/diastolic direction and the computed motion component of the direction such as twist or rotation are displayed on the display unit 307.

As thus described, according to the third embodiment of the present invention, it becomes possible to obtain motion components which are more effective in diagnosis by setting a cardiac systole/diastolic direction manually and computing an exercise component of the cardiac systole/diastolic direction or a motion component of a direction such as twist or rotation.

According to the present invention, since a motion component of a direction such as twist or rotation different from the cardiac systole/diastolic direction can be measured along with the motion component of the cardiac systole/diastolic direction, the motion component, which is more effective in diagnosis can be acquired.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical kinematic analysis apparatus, including a processor, to analyze a cardiac motion from time series image data obtained by capturing a heart, comprising:
    a tracking point coordinate acquiring unit configured to generate coordinate time series data indicating a coordinate of a tracking point on a heart from time series image data obtained by capturing the heart;
    an image data storing unit that stores the time series image data;
    a motion information acquiring unit configured to generate time series motion information of the tracking point from the coordinate time series data;
    a contour extraction unit configured to extract a cardiac contour of the heart from the time series image data;
    a direction acquiring unit configured to acquire a first cardiac motion direction in a normal direction with respect to the cardiac contour at a point on the cardiac contour nearest to the tracking point and a second cardiac motion direction in a tangential direction with respect to the cardiac contour at the point on the cardiac contour nearest to the tracking point;
    a first motion component computation unit configured to compute a first motion component of the first cardiac motion direction from the time series motion information; and
    a second motion component computation unit configured to compute a second motion component of the second cardiac motion direction from the time series motion information.

2. The apparatus according to claim 1, wherein the direction acquiring unit comprises a direction setting unit configured to set the first cardiac motion direction and the second cardiac motion direction,
    the first motion component computation unit is configured to compute the first motion component of the first cardiac motion direction set by the direction setting unit from the time series motion information; and
    the second motion component computation unit is configured to compute the second motion component of the second cardiac motion direction perpendicular to the first cardiac motion direction from the time series motion information.

3. The apparatus according to claim 1, wherein the second motion component computation unit computes the second motion component of a direction of a cardiac twist or rotation from the time series motion information.

4. The apparatus according to claim 1, which further comprises a display to display the motion component of the first motion component computation unit and the motion component of the second component computation unit.

5. The apparatus according to claim 1, wherein the time series motion information of the tracking point is time series data of the velocity vector of the tracking point.

6. The apparatus according to claim 1, wherein the time series motion information of the tracking point is time series data of displacement vector of the tracking point.

7. A medical kinematic analysis method implemented by a computer programmed as a medical kinematic analysis apparatus for analyzing a cardiac motion from time series image data obtained by capturing a heart, comprising:
    generating coordinate time series data indicating a coordinate of a tracking point on the heart from the time series image data;
    generating time series motion information of the tracking point from the coordinate time series data;

extracting a cardiac contour of the heart from the time series image data;

acquiring a first cardiac motion direction in a normal direction with respect to the cardiac contour at a point on the cardiac contour nearest to the tracking point and a second cardiac motion direction in a tangential direction with respect to the cardiac contour at the point on the cardiac contour nearest to the tracking point;

computing, by a processor of the computer, a first motion component of the normal direction from the time series motion information; and computing a second motion component of the tangential direction from the time series motion information.

8. The method according to claim 7, wherein the acquiring step includes setting the normal direction and the tangential direction, the step of computing the first motion component includes computing the first motion component of the normal direction set by the setting from the time series motion information; and the step of computing the second motion component includes computing the second motion component of the tangential direction perpendicular to the normal direction from the time series motion information.

9. The method according to claim 7, wherein the step of computing the second motion component includes computing the second motion component of a direction of a cardiac twist or rotation from the time series motion information.

10. The method according to claim 7, further comprising:

displaying the first motion component and the second motion component.

11. The method according to claim 7, wherein the time series motion information of the tracking point is time series data of the velocity vector of the tracking point.

12. The method according to claim 7, wherein the time series motion information of the tracking point is time series data of a displacement vector of the tracking point.

* * * * *